United States Patent
Sellers

(10) Patent No.: US 10,912,596 B2
(45) Date of Patent: Feb. 9, 2021

(54) ARTHRODESIS COMPRESSION DEVICE

(71) Applicant: Daniel Sellers, Salt Lake City, UT (US)

(72) Inventor: Daniel Sellers, Salt Lake City, UT (US)

(73) Assignee: Daniel Sellers, Draper, UT (US)

( * ) Notice: Subject to any disclaimer, the term of this patent is extended or adjusted under 35 U.S.C. 154(b) by 231 days.

(21) Appl. No.: 15/586,262

(22) Filed: May 3, 2017

(65) Prior Publication Data
US 2018/0317989 A1     Nov. 8, 2018

Related U.S. Application Data

(63) Continuation-in-part of application No. 14/257,981, filed on Apr. 21, 2014, now abandoned.

(60) Provisional application No. 61/814,584, filed on Apr. 22, 2013.

(51) Int. Cl.
| A61B 17/86 | (2006.01) |
| A61B 17/72 | (2006.01) |
| A61B 17/68 | (2006.01) |

(52) U.S. Cl.
CPC ........ *A61B 17/864* (2013.01); *A61B 17/7291* (2013.01); *A61B 17/8685* (2013.01); *A61B 17/7225* (2013.01); *A61B 2017/681* (2013.01)

(58) Field of Classification Search
CPC .................. A61B 17/7291; A61B 17/8685
See application file for complete search history.

(56) References Cited

U.S. PATENT DOCUMENTS

| 5,827,285 A  * | 10/1998 | Bramlet ................. A61B 17/68 606/60 |
| 2010/0016903 A1* | 1/2010 | Matityahu ............ A61B 17/866 606/301 |

* cited by examiner

*Primary Examiner* — Andrew Yang
(74) *Attorney, Agent, or Firm* — Kirton McConkie; Alexis V. Nelson

(57) ABSTRACT

A device for compression in arthrodesis is provided. The device is generally comprised of two screws, a proximal screw and a distal screw, the distal screw being configured to connect to the proximal screw. The proximal screw may have two portions, one portion with external bone threads, and one terminal portion. The two portions of the proximal screw may be formed such that they form an angle desirable for arthrodesis, or permanent fixation, of the joint. The distal screw may be inserted into the proximal screw, and may be further provided with additional external bone threads to provide compression at the joint site.

18 Claims, 7 Drawing Sheets

ARTHRODESIS COMPRESSION DEVICE

BACKGROUND OF THE INVENTION

1. The Field of the Invention

The present invention relates generally to bone screws. More specifically, the present invention relates to a bone screw for drawing together portions of a bone.

2. State of the Art

Arthrodesis is the artificial induction of joint ossification between two bones via surgery. Arthrodesis is often performed to relieve intractable pain in a joint which cannot be managed by pain medication, splints, or other generally-indicated treatments. The typical causes of such pain are arthritis and fractures or injuries which disrupt the joint.

Arthrodesis is the most common form of surgical treatment for osteoarthritis of the distal inter-phalangeal (DIP) joint once non-operative management is no longer effective. If a patient has severe arthritis or destructive trauma of the DIP joint, it may be beneficial to fuse the DIP joint in a fixed position. Arthrodesis improves appearance, corrects deformity and instability, and, as a result of pain relief, increases strength and function. The trade-off, cessation of joint range of motion at the DIP joint, is generally not considered to be a severe functional limitation.

The goal of any arthrodesis is a stable bony union in a proper position within a reasonable period of time. Many techniques of varying complexity have been described for DIP arthrodesis. Generally, surgical treatment of an arthritic joint involves an incision over the joint (on the dorsal aspect of the finger) and removal of the actual joint surface. Usually these joint surfaces (one on each bone involved in the joint) are degenerated. It may be best to fuse the joint at about a 20-degree to 30-degree angle so as to allow use of the finger in a more natural and useful posture. In order to do this, the articular surfaces of the joint are removed down to cancellous bone, such that there are flat surfaces on the bones that can be approximated to effect true bone-to-bone healing. In order for these surfaces to heal together optimally, they must be immobilized and compressed together during the healing process. According to the prior art, this is done with either straight compression screws, or K-wires (straight pins that are drilled through the bone that give immobilization but no compression). Achieving and maintaining immobilization and compression of the DIP joint of the finger in an angled position for arthrodesis can be difficult and is prone to instability.

SUMMARY OF THE INVENTION

An arthrodesis compression device is provided for applying compression, the device having a proximal screw and a distal screw, wherein the proximal screw may have an internally threaded portion. The distal screw is configured for insertion into the internally threaded portion of the proximal screw.

According to one configuration, the device may have a proximal screw that includes bone threads of varying pitch and diameter for providing anchoring into one of the two bones to be arthrodesed. The proximal screw may include an internally threaded hollow to receive external threads on the distal screw.

According to another configuration, the proximal screw may be formed at an angle such that the joint is fused together at an angle. The angle may be formed at any angle desired, and may vary depending on the needs of the particular patient. The proximal screw may also be formed without an angle to allow joint fusion in a generally straight line.

According to another configuration, the proximal screw may include a nose portion and a terminal portion. Each of the nose portion and the terminal portion of the proximal screw may have a long axis, and the long axis of the nose portion may be offset from (i.e., not parallel to) the long axis of the terminal portion.

According to another configuration, the arthrodesis compression device may include bone threads on the distal screw for providing further compression.

According to another configuration, the distal screw of the device may be provided with a screw head. In yet another configuration, the distal screw may not include a screw head. In yet another configuration, the distal screw may be provided with bone threads.

These and other aspects of the present invention are realized in an arthrodesis compression device as shown and described in the following figures and related description. It will be appreciated that various configurations of the invention may not include each aspect set forth above and aspects discussed above shall not be read into the claims unless specifically described therein.

BRIEF DESCRIPTION OF THE DRAWINGS

Various configurations of the present invention are shown and described in reference to the numbered drawings, all of which are drawn on an oversized scale, wherein.

Figure 1:
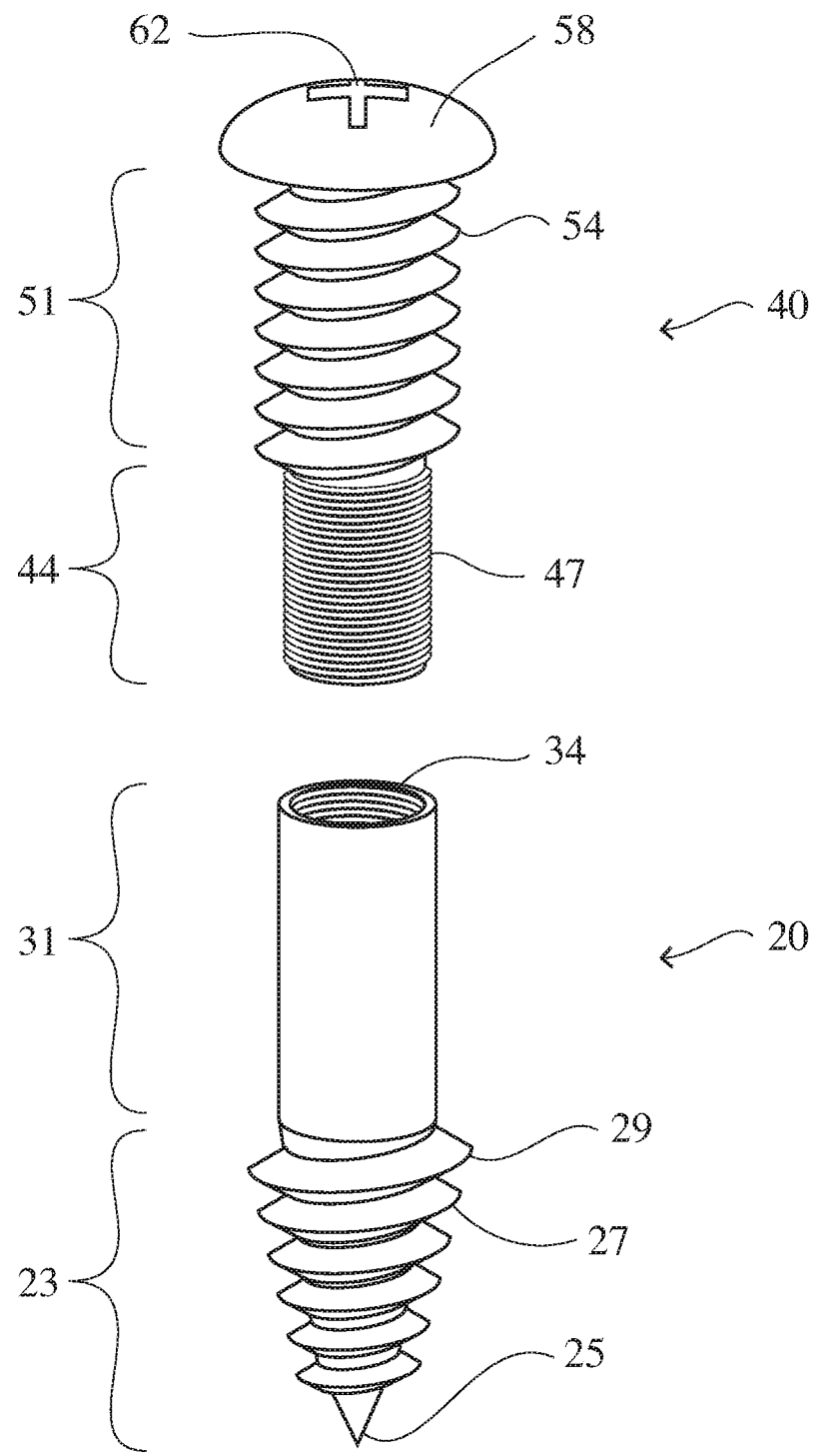
FIG. 1 shows a side perspective elevation of a compression device according to one aspect of the disclosure.

It will be appreciated that the drawings are illustrative and not limiting of the scope of the invention which is defined by the appended claims. The configurations shown accomplish various aspects and objects of the invention. It is appreciated that it is not possible to clearly show each element and aspect of the invention in a single figure, and as such, multiple figures are presented to separately illustrate various details of the invention in greater clarity. Thus, it will be appreciated that aspects shown in the drawings separately may be combined. Similarly, not every configuration need accomplish all advantages or aspects of the present invention.

DETAILED DESCRIPTION

The invention and accompanying drawings will now be discussed in reference to the numerals provided therein so as to enable one skilled in the art to practice the present invention. The skilled artisan will understand, however, that the apparatuses, systems and methods described below can be practiced without employing these specific details, or that they can be used for purposes other than those described herein. Indeed, they can be modified and can be used in conjunction with products and techniques known to those of skill in the art in light of the present disclosure. The drawings and descriptions are intended to be exemplary of various aspects of the invention and are not intended to narrow the scope of the appended claims. Furthermore, it will be appreciated that the drawings may show aspects of the invention in isolation and the elements in one figure may be used in conjunction with elements shown in other figures.

Reference in the specification to "one configuration" or "a configuration" means that a particular feature, structure, or characteristic described in connection with the configuration is included in at least one configuration, but is not a requirement that such feature, structure or characteristic be present in any particular configuration unless expressly set forth in the claims as being present. The appearances of the phrase "in one configuration" in various places may not necessarily limit the inclusion of a particular element of the invention to a single configuration, rather the element may be included in other or all configurations discussed herein.

Furthermore, the described features, structures, or characteristics of configurations of the invention may be combined in any suitable manner in one or more configurations. In the following description, numerous specific details are provided, such as examples of products or manufacturing techniques that may be used, to provide a thorough understanding of configurations of the invention. One skilled in the relevant art will recognize, however, that configurations of the invention may be practiced without one or more of the specific details, or with other methods, components, materials, and so forth. In other instances, well-known structures, materials, or operations are not shown or described in detail to avoid obscuring aspects of the invention.

Before the present invention is disclosed and described in detail, it should be understood that the present disclosure is not limited to any particular structures, process steps, or materials discussed or disclosed herein, but is extended to include equivalents thereof as would be recognized by those of ordinarily skill in the relevant art. More specifically, the invention is defined by the terms set forth in the claims. It should also be understood that terminology contained herein is used for the purpose of describing particular aspects of the invention only and is not intended to limit the invention to the aspects or configurations shown unless expressly indicated as such. Likewise, the discussion of any particular aspect of the invention is not to be understood as a requirement that such aspect is required to be present apart from an express inclusion of the aspect in the claims.

It should also be noted that, as used in this specification and the appended claims, singular forms such as "a," "an," and "the" may include the plural unless the context clearly dictates otherwise. Thus, for example, reference to "a spring" may include one or more of such springs, and reference to "the layer" may include reference to one or more of such layers.

As used herein, the term "substantially" refers to the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing the nearly all of the length of a lumen would be substantially enclosed, even if the distal end of the structure enclosing the lumen had a slit or channel formed along a portion thereof. The use of "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it lacked a bottom.

As used herein, the term "about" is used to provide flexibility to a numerical range endpoint by providing that a given value may be "a little above" or "a little below" the endpoint while still accomplishing the function associated with the range.

As used herein, a plurality of items, structural elements, compositional elements, and/or materials may be presented in a common list for convenience. However, these lists should be construed as though each member of the list is individually identified as a separate and unique member.

Concentrations, amounts, proportions and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described Turning now to FIG. 1, a perspective side elevation view of an arthrodesis compression device according to one configuration is shown. The device is comprised of a proximal screw, generally indicated at 20, and a distal screw, generally indicated at 40. In use, as described in additional detail below, the distal screw 40 is configured to be inserted into the proximal screw 20. In some configurations, the distal screw 40 is configured to be inserted into the proximal screw 20 by screwing the distal screw 40 into the proximal screw 20. In other configurations, the distal screw 40 and proximal screw 20 may be connected through other means known in the art, such as a ball and socket, etc. Additionally, the threads of the screws may be of varying pitch and diameter.

The proximal screw 20 has a nose portion 23 and a terminal portion 31. The nose portion 23 may be conical in shape and have external threads, for example external threads 27 and 29. The external threads may be provided, for example, to achieve secure anchoring of the nose portion 23 of the device into the medullary canal of the distal end of a middle phalanx of a patient. In other configurations, the nose portion 23 may be cylindrical in shape, or any other suitable shape.

The terminal portion 31 of the proximal screw 20 includes an internally threaded hollow cylinder. It is not necessary for the entire length of the terminal portion 31 to be hollow and internally threaded; a section near the nose portion 23 of the proximal screw 20 may be solid, for example. The internal threads 34 of the terminal portion 31 are configured for mating with the external threads 47 on the leading portion 44 of the distal screw 40, as described in detail below. The terminal portion 31, of the proximal screw 20, by way of example, may be between about 5 and 8 millimeters long for the fusion of a DIP joint. The terminal portion may be formed of any desired length, and could be formed longer or shorter depending on the specific needs of a particular patient.

The distal screw, generally indicated at 40, includes a leading portion 44 and a trailing portion 51. The leading portion 44 has external threads 47. These external threads 47 are like-handed to and have a similar pitch to the internal threads 34 on the terminal portion 31 of the proximal screw 20. External threads 47 are configured for mating with internal threads 34.

The trailing portion 51 of the distal screw 40 may be a cylinder. The trailing portion 51 may include external threads 54. External threads 54 may be configured to have a larger radial circumference than external threads 47, or external threads 54 may have a more aggressive pitch than external threads 47. In some configurations, external threads 54 may have a larger radial circumference and a more aggressive pitch than external threads 47. Larger circumferenced-threads may allow for additional engagement in bones to be attached through arthrodesis. A differentially wider pitch of external threads 54 compared to the external threads 47 may allow for additional compressive forces across the arthrodesis, and/or greater security of the distal screw 40 within the bone.

The distal screw 40 may also be provided with a screw head 58, and a slot 62 to accommodate a tool for driving the screw, such as a screw driver or the like. Slot 62 could be of any shape or depth appropriate for accommodating a tool to drive the screw such as an allen wrench, or alternatively may be a projection that can engage a tool for driving the screw, such as a socket wrench, etc. In one configuration, the screw head 58 is configured to be drilled down into the bone of the distal phalanx.

Figure 2:
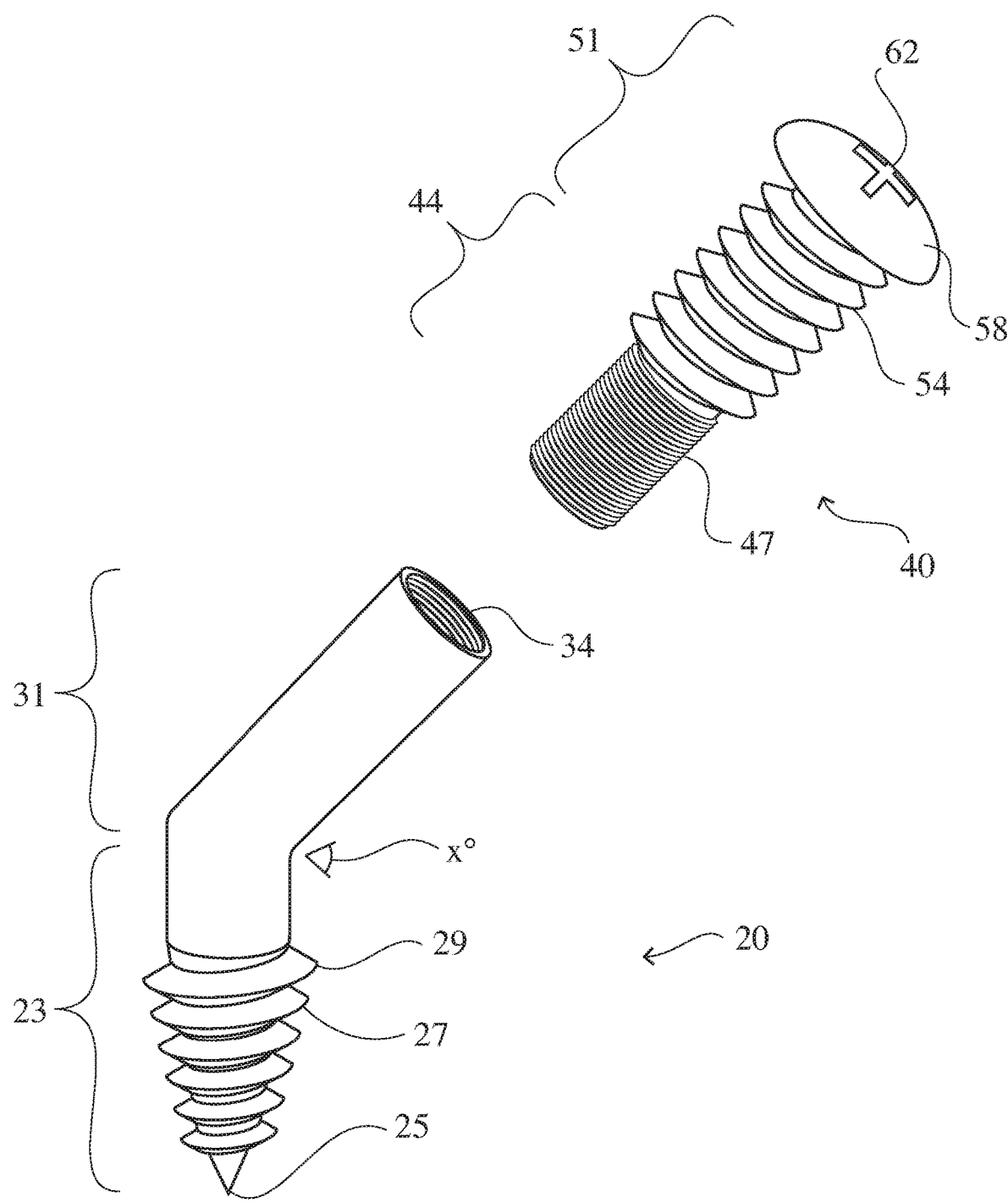
FIG. 2 shows a side perspective elevation of a compression device according to another aspect of the disclosure.

Turning now to FIG. 2, there is shown another configuration of the compression device. In this configuration, the proximal screw 20 includes a nose portion 23 and a terminal portion 31. The nose portion 23 and the terminal portion 31 are connected (or formed integrally) such that they form an angle x°. In other words, the terminal portion 31 and the nose portion 23 each have a long axis, and the long axis of the nose portion 23 may be offset from the long axis of the terminal portion 31. The angle x° may be any angle desirable. The angle x° formed by the nose portion 23 and the terminal portion 31 may be the angle between the middle phalanx and the distal phalanx of the patient, as described below, when the arthrodesis compression device is used in vivo. This angle may be varied depending on the individual patient's needs. For example, the angle may be between about 15 degrees and 45 degrees. The distal screw 40 is configured to be connected to the proximal screw 20 in a similar manner as described above, with the external threads 47 of the distal screw 40 configured to mate with the internal threads 34 of the proximal screw 20. Furthermore, the proximal screw 20 and distal screw 40 may be joined together according to other methods, such as a locking mechanism with a ball and socket, or any other joining or locking methods known in the art. For example, other double screw configurations known in the art could be used.

Figure 3:
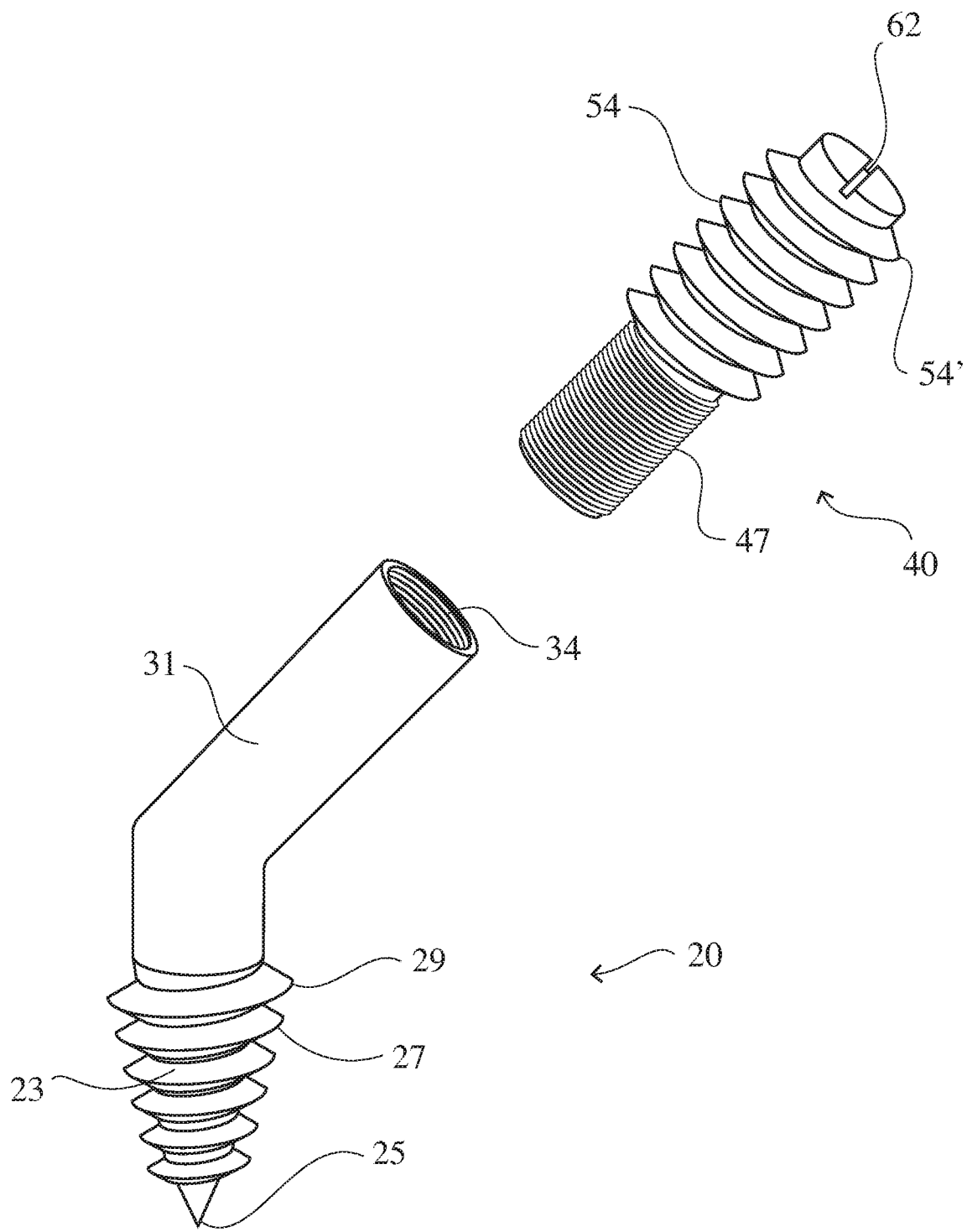
FIG. 3 shows a side perspective elevation of a compression device according to another aspect of the disclosure.

Turning now to FIG. 3, there is shown another configuration of the arthrodesis compression device, wherein the distal screw 40 may be configured such that there is no screw head. Depending on a surgeon's preferences, a screw head may be less desirable because it may cause a concentrated load and protrude after the screw is installed. For example, the distal screw 40 may have external bone threads 54 which are larger in diameter than external threads 47. Thus, the crest diameter 54' of the external bone threads would be greater than the diameter of any other part of the distal screw, and the crest diameter 54' may be able to engage the inside of the bone, or become lodged within the bone. External bone threads 54 may engage the bone such that a traditional screw head would not be necessary, and the distal screw may be entirely encased in the bone. One having skill in the art will appreciate that the distal screw could be formed in various manners according to the present disclosure, such as with a screw head but no bone threads, with bone threads but no screw head, with both bone threads and a screw head, etc.

Figure 4:
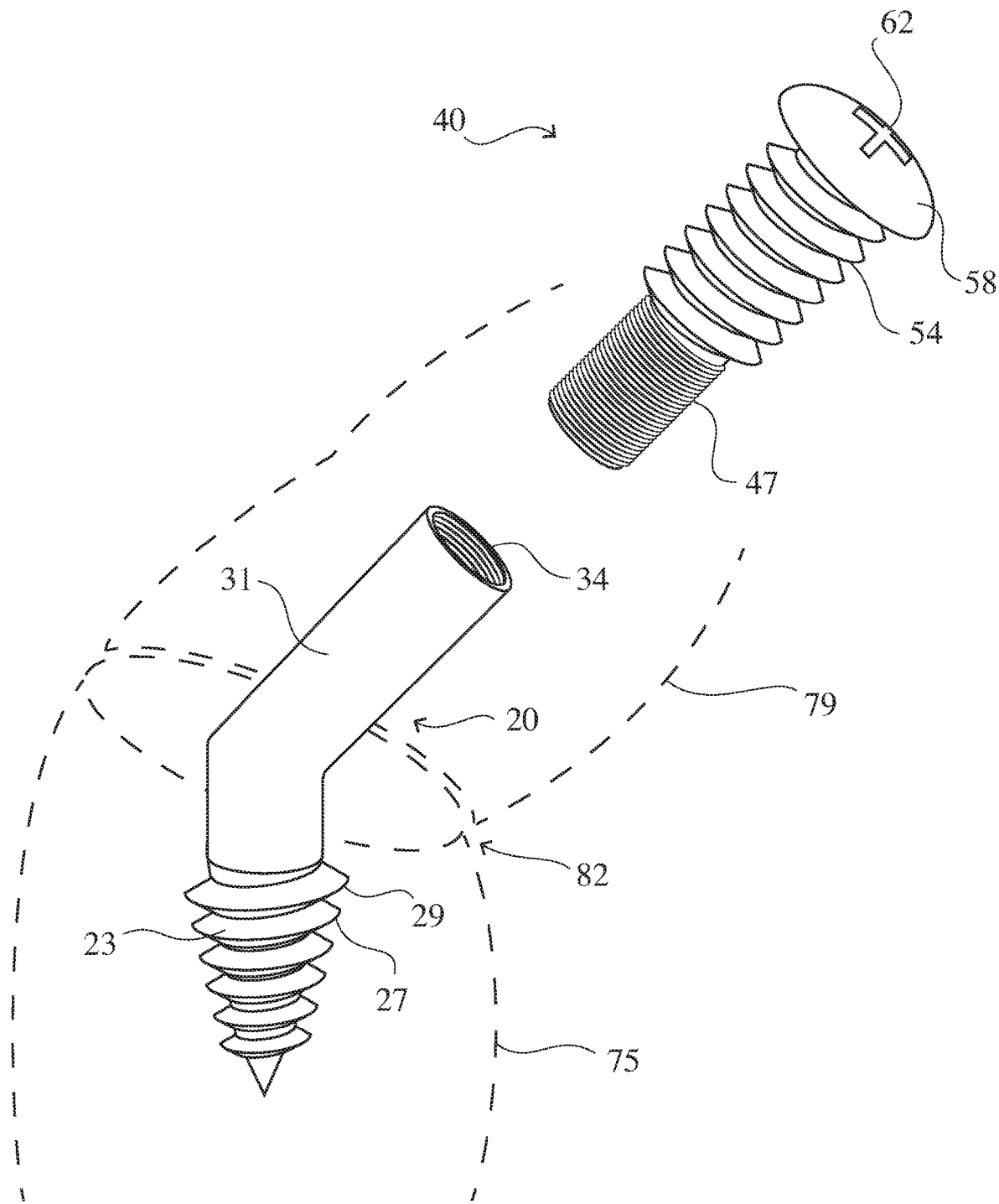
FIG. 4 shows a side perspective elevation of the compression device of FIG. 2 being used in an arthrodesis of a middle phalanx and a distal phalanx (shown in dashed lines)

The arthrodesis compression device disclosed herein has many applications, and one of the numerous examples will be discussed in detail herein. One having skill in the art will appreciate the numerous other applications of the device. By way of example, the device may be deployed to assist the arthrodesis of the DIP joint of a finger. FIG. 4 shows a configuration of the device, with an approximately 30-degree angle between the terminal portion 31 and the nose portion 23 of the proximal screw 20, as it would be inserted for arthrodesis of a DIP joint between the middle phalanx 75 and the distal phalanx 79.

In use for a DIP joint, the surgeon may screw the nose portion 23 of the proximal screw 20 into the medullary canal of the distal end of the middle phalanx 75 (depending on the patient, this may or may not require pre-drilling of the medullary canal). This would leave the terminal portion 31 of the proximal screw extending about 5 to 8 millimeters from the cut surface of the middle phalanx 75 (depending on the length of the terminal portion 31, which may be configured to be a standard length, or in other configurations may be varied based on the particular patient's needs).

If the surgeon desires to fuse the joint at a permanent angle, a proximal screw 20 with the desired angle between the leading portion 23 and the terminal portion 31 may be used. A hole may then be drilled axially through the distal phalanx 79 and the distal screw 40 may be placed through the finger tip of the distal phalanx 79. By way of example, this hole may be about two millimeters to three millimeters in diameter; for example, the hole may be large enough to allow the terminal portion 31 of the proximal screw to pass through, and narrow enough to allow bone threads 54, if provided, to engage the inner surface of the bone. The distal screw 40 may be turned via slot 62 such that external threads 47 of the distal screw 40 engage the internal threads 34 of the proximal screw 20.

If the distal screw 40 is also provided with bone threads 54, the bone threads 54 may engage the surrounding bone of the distal phalanx 79 as the distal screw 40 is turned. These bone threads 54 may be slightly more aggressive than the external threads 47 that engage the terminal portion 31, such that as the distal screw 40 is tightened it is advanced into the hollow terminal portion 31 of the proximal screw 20, and the bone of the distal phalanx 79 is also advanced such that there is compression of the distal phalanx 79 to the middle phalanx 75 at the joint site 82. This may achieve the close apposition of bone in arthrodesis that is important to effective healing.

Figure 5:
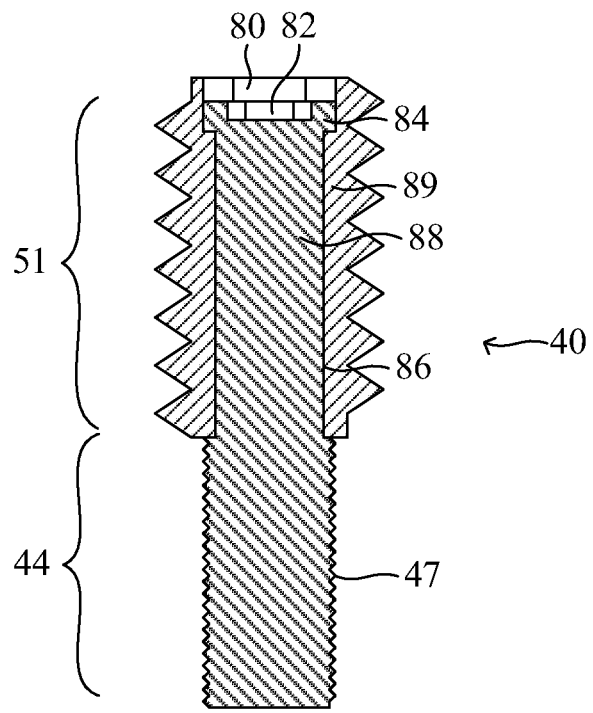
FIG. 5 shows one embodiment of an arthrodesis compression device comprising a distal screw having a leading portion that rotates independently from a trailing portion.
Figure 5:
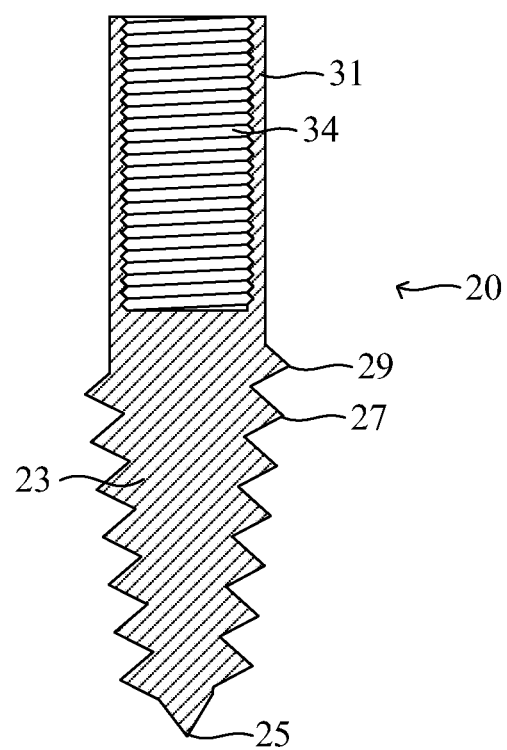

Referring to FIG. 5, in certain embodiments, an arthrodesis compression device in accordance with the invention may be configured to enhance compression and/or proximity between bone surfaces. This, in turn, may improve the ability of the arthrodesis compression device to induce arthrodesis between the bone surfaces. For example, in certain embodiments, the distal screw 40 may be designed such that a leading portion 44 and trailing portion 51 rotate independently from one another. This may allow the proximal screw 20 to be initially driven into a first bone of a patient using external threads (typically course bone threads) of the nose portion 23. The distal screw 40 may then be driven into and engage a second bone of a patient using external threads (typically course bone threads) of the trailing portion 51. The proximal screw 20 and distal screw 40 may be driven into their respective bones such that the bones achieve a desired angle relative to one another.

Once the proximal screw 20 and distal screw 40 are in place in their respective bones, the leading portion 44 may then be rotated independently of the trailing portion 51 to thread (using, for example, fine machine threads) the leading portion 44 into a terminal portion 31 of the proximal screw 20. This will bring the distal screw 40 and proximal screw 20 (and associated bones in which they are engaged) together. The ability to rotate the leading portion 44 of the distal screw 40 independently from the trailing portion 51 may enable adjustment of the amount of compression and/or proximity between the bone surfaces. If desired, some mechanism (glue, mechanical locks, etc.) may be used to lock the leading portion 44 in place relative to the trailing portion 51 after a desired amount of compression or proximity is achieved.

As shown in FIG. 5, in certain embodiments, the leading portion 44 and trailing portion 51 of the distal screw 40 may each have a separate head or socket that allows them to be rotated independently by a tool. In the illustrated embodiment, each of the leading portion 44 and trailing portion 51 have different sized sockets 80, 82 to receive hex keys of different sizes. The hex socket 82 of the leading portion 44 may be accessed through the hex socket 80 of the trailing portion 51. Other types of sockets or structures for rotating the leading portion 44 and trailing portion 51 are possible and within the scope of the invention.

In the embodiment illustrated in FIG. 5, the trailing portion 51 is embodied as a sleeve and the leading portion 44 is embodied as a pin that at least partially passes through the sleeve. In this embodiment, the leading portion 44 is not removable from the trailing portion 51 by virtue of the head 84 on the pin 88 and the larger circumference of the external threads 47 relative to the internal diameter 86 of the sleeve 89. This will keep the leading portion 44 retained within the trailing portion 51. In other embodiments, it is contemplated that the leading portion 44 could be removed or separated from the trailing portion 51 as needed or desired. This could be accomplished, for example, by making the circumference of the external threads 47 of the leading portion 44 smaller than the inside diameter 86 of the trailing portion 51. Such an embodiment may enable the trailing portion 51 to be initially installed in bone, afterwhich the leading portion 44 may be inserted through the trailing portion 51 to be threaded into the terminal portion 31 of the proximal screw 20.

The arthrodesis compression device of FIG. 5 may be modified in various ways without departing from various characteristics or principles of the invention as described herein. For example, the leading portion 44 is shown with external threads and the terminal portion 31 is shown with internal threads. This could be easily switched so that the leading portion 44 includes internal threads that mate with external threads of the terminal portion 31. Similarly, the arthrodesis compression device of FIG. 5 may be modified to have an angle like the device illustrated in FIG. 4, or other features associated with the devices illustrated in FIGS. 1-4. Other variations are possible and within the scope of the invention.

Figure 6:
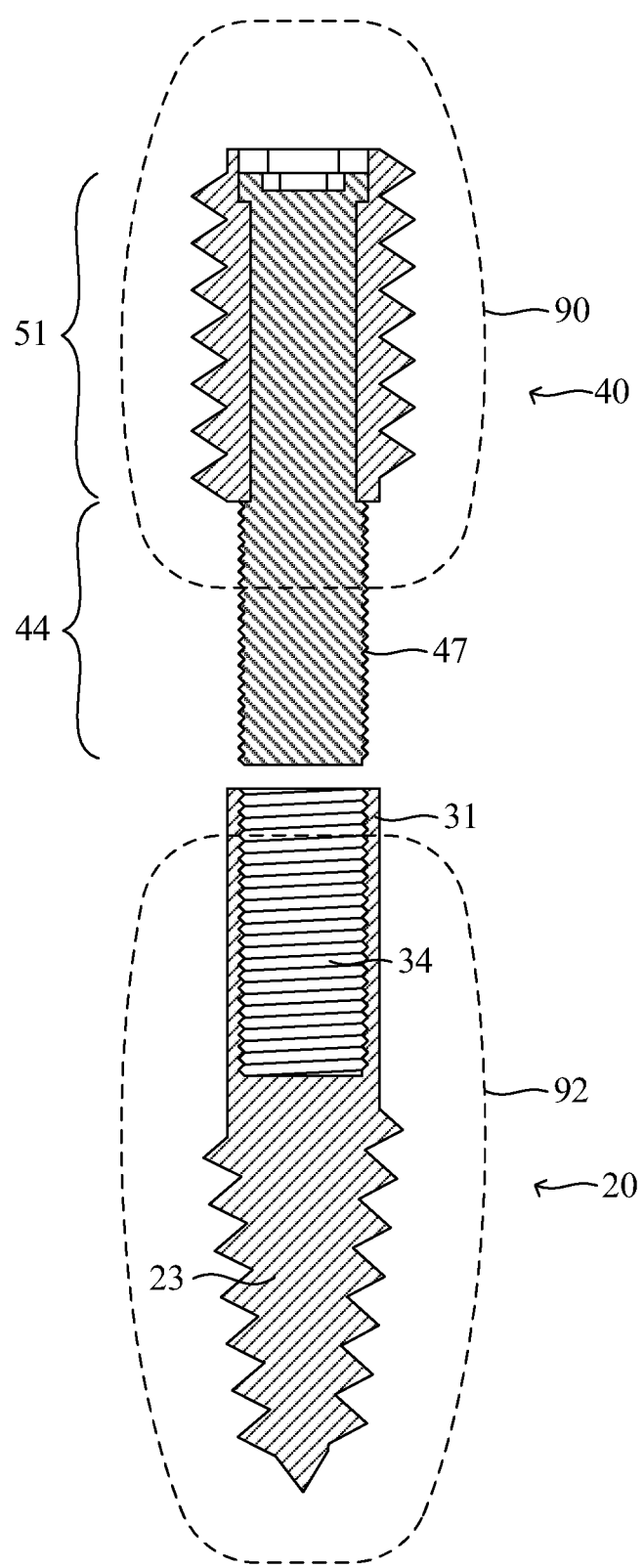
FIG. 6 shows placement of the proximal screw and distal screw into two different bones of a patient.
Figure 7:
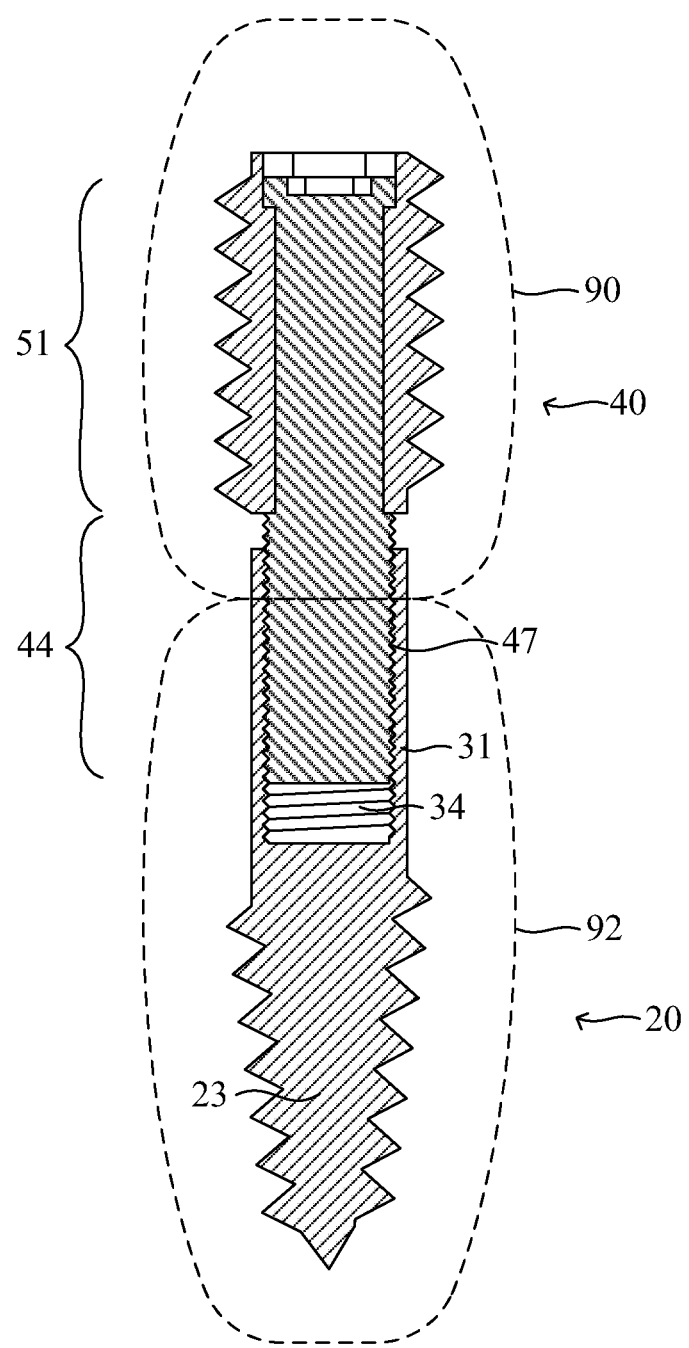
FIG. 7 shows how the arthrodesis compression device of FIG. 5 and FIG. 6 may be used to draw bones together.

Referring to FIG. 6 and FIG. 7, a method for fusing two bones 90, 92 together using the arthrodesis compression device of FIG. 5 is illustrated. The method is presented by way of example and not limitation. Various of the steps presented herein may be altered, performed in a different order, removed, or performed with other steps not described herein.

As shown in FIG. 6, to achieve the benefits of the disclosed arthrodesis compression device, the proximal screw 20 of the arthrodesis compression device may be initially driven into a first bone 92 of a patient. In certain embodiments, a hole may be drilled in the first bone 92 prior to driving in the proximal screw 20. The proximal screw 20 may, in certain embodiments, be driven into the first bone 92 sufficient to leave the terminal portion 31 extending some desired length (e.g., 5 to 8 millimeters) from the first bone 92.

The distal screw 40 may then be driven into a second bone 90 that is to be ossified with the first bone 92. In certain cases, a hole may be drilled in the second bone 90 prior to driving in the distal screw 40. In certain embodiments, the distal screw 40 is driven into the second bone 90 to a desired depth in its entirety (both the leading portion 44 and trailing portion 51 are driven into the second bone 90 together). In other embodiments, namely embodiments where the leading portion 44 is removable from the trailing portion 51, only the trailing portion 51 is initially driven into the second bone 90. The leading portion 44 may then be inserted into the trailing portion 51 so that it extends from the trailing portion 51.

The leading portion 44 may then be rotated independently from the trailing portion 51 to thread the leading portion 44 into the terminal portion 31 of the proximal screw 20. This will urge the proximal screw 20 towards the distal screw 40. This may continue until the first bone 92 is adjacent to the second bone 90 and/or a desired amount of compression is achieved. If desired, some mechanism (glue, mechanical locks, etc.) may be used to prevent rotation of the leading portion 44 relative to the trailing portion 51 once the desired amount of compression or proximity is achieved.

An arthrodesis compression device may include: a proximal screw, the proximal screw including a nose portion having external threads and a terminal portion; and a distal screw, the distal screw including a leading portion and a trailing portion wherein the leading portion of the distal screw is configured to be connected to the terminal portion of the proximal screw. The terminal portion of the proximal screw may have an internally-threaded hollow cylinder. The leading portion of the distal screw may have external threads.

In one configuration, the leading portion of the distal screw may be configured to be connected to the terminal portion of the proximal screw through a ball and socket.

The internal threads of the terminal portion of the proximal screw may be configured for mating with the external threads of the leading portion of the distal screw. The nose portion and the terminal portion of the proximal screw may be offset at an angle. For example, the angle may be between about 25 degrees and 35 degrees.

The terminal portion of the proximal screw may be between about 5 and 8 millimeters long. The trailing portion of the distal screw may include external threads. The leading portion of the distal screw may include external threads, the external threads of the trailing portion of the distal screw having a larger circumference than the external threads of the leading portion of the distal screw. The external threads of the trailing portion of the distal screw may also have a shallower pitch. The distal screw may also include a screw head.

A device for providing compression in arthrodesis is disclosed, the device including: a proximal screw, the proximal screw having a nose portion and a terminal portion; the nose portion having external threads, and the terminal portion being comprised of an internally-threaded hollow cylinder; and a distal screw, the distal screw having a leading portion and a trailing portion, the leading portion comprising external threads configured to mate with the internally-threaded hollow cylinder of the terminal portion of the proximal screw, and the trailing portion having externally threaded bone threads.

The nose portion and the terminal portion of the proximal screw each may have a long axis and wherein the long axis of the nose portion is offset from the long axis of the terminal portion at an angle. The angle may be between about 15 degrees and 45 degrees. The nose portion of the proximal screw may further have a tip, and wherein the external threads of the nose portion have a pitch designed to achieve secure fixation into a medullary canal. The terminal portion of the proximal screw may be any desired length; in one configuration, the length may be between about 5 and 8 millimeters long for DIP fusion. The trailing portion of the distal screw may comprise external bone threads, with the external bone threads of the trailing portion of the distal screw having a larger circumference than the external threads of the leading portion of the distal screw with a differential pitch designed for bone compression. The distal screw may also include a screw head.

A method for fusing two bones together is disclosed, the method comprising: disposing a first screw into a first bone to be fused such that the first screw is anchored in the first bone by external threads on the first screw, and into a second bone to be fused to the first bone such that a portion of the first screw having internal threads is disposed in the second bone; and attaching a second screw to the internal threads of the first screw to anchor the first screw into the second bone. According to this method, the first screw may have a nose portion and a terminal portion, which are offset at an angle relative to one another.

According to this method, the second screw may include a leading portion with external threads and a trailing portion with external threads, the external threads of the trailing portion having a larger circumference than the external threads of the leading portion. The second screw may also include a projection or slot disposed thereon for accommodating a tool to drive the screw.

There is thus disclosed an improved arthrodesis compression device. It will be appreciated that numerous changes may be made to the present invention without departing from the scope of the claims.

The invention claimed is:

1. An arthrodesis compression device comprising:
   a proximal screw comprising a nose portion having external bone threads and a terminal portion, wherein a long axis of the nose portion and a long axis of the terminal portion are offset at an angle; and
   a distal screw comprising a leading portion and a trailing portion that rotate independently from one another around a common axis while maintaining a substantially fixed position relative to one another along the common axis, wherein the leading portion of the distal screw is configured to connect to the terminal portion of the proximal screw.

2. The arthrodesis compression device of claim 1, wherein the terminal portion of the proximal screw comprises internal threads.

3. The arthrodesis compression device of claim 2, wherein the leading portion of the distal screw comprises external threads that thread into the internal threads of the terminal portion.

4. The arthrodesis compression device of claim 3, wherein the trailing portion of the distal screw comprises external bone threads.

5. The arthrodesis compression device of claim 4, wherein the external bone threads of the trailing portion have a larger diameter than the external threads of the leading portion.

6. The arthrodesis compression device of claim 4, wherein the external bone threads of the trailing portion have a greater pitch than the external threads of the leading portion.

7. The arthrodesis compression device of claim 3, wherein the external threads of the leading portion comprise a larger circumference than an internal diameter of the trailing portion.

8. The arthrodesis compression device of claim 1, wherein the angle is between about 0 and 45 degrees.

9. The arthrodesis compression device of claim 1, wherein the trailing portion is embodied as a sleeve and the leading portion is embodied as a pin that at least partially passes through the sleeve.

10. The arthrodesis compression device of claim 1, wherein the leading portion is connected to the trailing portion.

11. An arthrodesis compression device comprising:
    a proximal screw comprising a nose portion having external threads and a terminal portion having internal threads, wherein a long axis of the nose portion and a long axis of the terminal portion are offset at an angle; and
    a distal screw comprising a leading portion having external threads and a trailing portion having external threads, wherein the leading portion and trailing portion rotate independently from one another around a common axis while maintaining a substantially fixed position relative to one another along the common axis, the trailing portion is embodied as a sleeve, and the leading portion is embodied as a pin that at least partially passes through the sleeve.

12. The arthrodesis compression device of claim 11, wherein the angle is between about 0 degrees and 45 degrees.

13. The arthrodesis compression device of claim 11, wherein the external threads of the nose portion and the external threads of the trailing portion are bone threads.

14. The arthrodesis compression device of claim 11, wherein the external threads of the trailing portion have a larger diameter than the external threads of the leading portion.

15. The arthrodesis compression device of claim 11, wherein the external threads of the trailing portion have a greater pitch than the external threads of the leading portion.

16. A method for fusing two bones together, the method including:
    driving a proximal screw into a first bone such that the proximal screw is anchored in the first bone by external threads on a nose portion of the proximal screw wherein a long axis of the nose portion and a long axis of a terminal portion of the proximal screw are offset at an angle;

driving a distal screw into a second bone such that the distal screw is anchored in the second bone by external threads on a trailing portion of the distal screw; and rotating a leading portion of the distal screw such that it threads into or over a terminal portion of the proximal screw, the leading portion of the distal screw rotating independently from the trailing portion of the distal screw around a common axis while maintaining a substantially fixed position relative to one another along the common axis, wherein rotating the leading portion causes the first bone to move towards the second bone.

17. The method of claim 16, wherein the trailing portion is embodied as a sleeve and the leading portion is embodied as a pin that at least partially passes through the sleeve.

18. The method of claim 16, wherein the external threads of the trailing portion have a greater pitch than external threads of the leading portion.

\* \* \* \* \*